United States Patent [19]

Libke et al.

[11] Patent Number: 4,895,163

[45] Date of Patent: Jan. 23, 1990

[54] SYSTEM FOR BODY IMPEDANCE DATA ACQUISITION

[75] Inventors: Al Libke, Los Angeles, Calif.; Richard G. Wooten, Tigard, Oreg.

[73] Assignee: Bio Analogics, Inc., Los Angeles, Calif.

[21] Appl. No.: 197,995

[22] Filed: May 24, 1988

[51] Int. Cl.$^4$ .................................................. A61B 5/05
[52] U.S. Cl. ...................................... 128/734; 128/639
[58] Field of Search ........................ 128/734, 774, 639; 364/413.02, 413.1; 324/65 R

[56] References Cited

U.S. PATENT DOCUMENTS

| | | | |
|---|---|---|---|
| 3,452,743 | 7/1969 | Rieke | 128/734 |
| 3,871,359 | 3/1975 | Pacela | 128/734 |
| 4,033,336 | 7/1977 | Murawski et al. | 128/774 |
| 4,154,114 | 5/1979 | Katz et al. | 364/413.02 |
| 4,459,995 | 7/1984 | Conners et al. | 128/734 |

FOREIGN PATENT DOCUMENTS 2753167  5/1979  Fed. Rep. of Germany ...... 128/734

Primary Examiner—Max Hindenburg
Assistant Examiner—Scott Getzow
Attorney, Agent, or Firm—Frank Frisenda, Jr.

[57] ABSTRACT

The unique system of the present invention provides an accurate valid measaurement of human body composition consisting of fat tissue, lean tissue and body water. The inventive methodology provides a procedure for quantitative measurement of the conductive potential of the body, which is based on the lean tissue content of the body, in a convenient and reliable manner. In more detail, the quantitative measurement in accordance with the present invention is referred to as a "bio-impedance signal." This electrical signal, in ohms, is derived from a means for measuring body impedance component of the system. The resultant signal (three digit number, between 1 and 1000 ohms) is then entered into a modifying means component to accurately predict the body composition of the tested individual. The unique modifying means, in one embodied form, comprises prediction formulas derived from biological data inputs including: a patient's height, weight, age and sex, to determine a "population prediction variable." Thus, the unique modifying means of the inventive system interprets bio-impedance readings as "population specific", i.e., specific impedance values are exhibited by various pre-defined populations of individuals. This specificity is related to morph-type, leanness, body water and age. In accordance with the present invention, an algorithm formula approach to prediction formulas is utilized to define an appropriate individual or set of variables.

7 Claims, 13 Drawing Sheets

BLOCK DIAGRAM

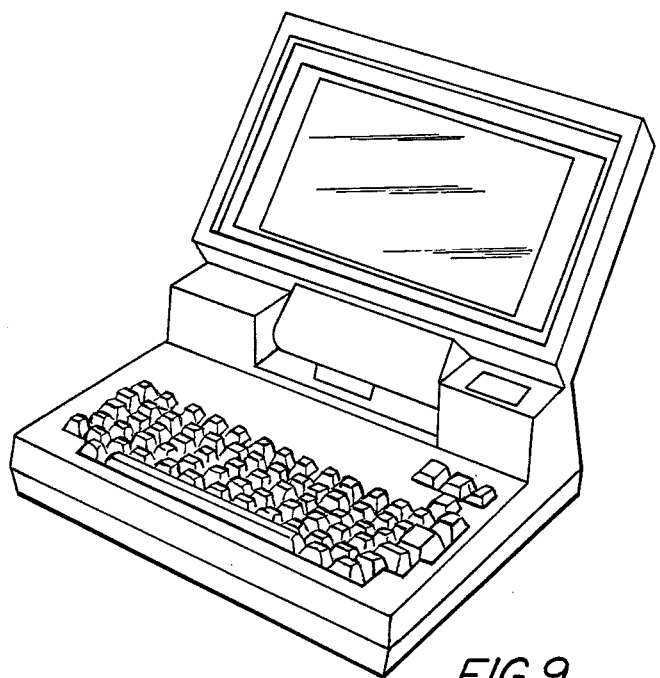

FIG. 9

INTER-METRE COMPARISONS

THE FOLLOWING SPREAD DATA SHEETS ARE THE RESULT OF AN "IN-HOUSE" STUDY TO DEMONSTRATE THE TEST RE-TEST RELIABILITY OF THE BID-OHM METRE PRODUCED BY BODY COMPOSITION ANALOG, INC. THE TESTING WAS DONE AT THE BEAVERTON, ORE. FACILITY.

SUBJECT GROUP A:

| Subject | Sex | Age | Height | Weight | Metre 1 | Metre 2 | Metre 3 |
|---|---|---|---|---|---|---|---|
| A | F | 22 | 64" | 110 lbs | 663 | 662 | 663 |
| B | M | 15 | 65" | 127 lbs | 593 | 593 | 590 |
| C | M | 17 | 72" | 183 lbs | 429 | 429 | 429 |
| D | F | 20 | 61" | 135 lbs | 650 | 649 | 652 |
| E | F | 17 | 62" | 125 lbs | 669 | 665 | 664 |
| F | F | 49 | 62" | 175 lbs | 571 | 572 | 571 |
| G | F | 26 | 64" | 100 lbs | 709 | 710 | 708 |
| H | M | 30 | 78" | 216 lbs | 441 | 439 | 442 |
| I | M | 26 | 72" | 190 lbs | 461 | 461 | 458 |
| J | F | 27 | 67.5" | 126 lbs | 512 | 516 | 513 |
| K | M | 21 | 68.75" | 188 lbs | 443 | 443 | 442 |
| L | M | 24 | 70" | 155 lbs | 388 | 388 | 385 |
| M | F | 28 | 64" | 132 lbs | 545 | 543 | 543 |
| N | F | 19 | 67.5" | 144 lbs | 617 | 616 | 620 |
| O | M | 33 | 70" | 188 lbs | 411 | 411 | 411 |
| P | F | 31 | 71" | 162 lbs | 656 | 654 | 656 |
| Q | M | 21 | 63" | 145 lbs | 587 | 588 | 587 |

Standard Individual Error: 2 OHMs

FIG. 11

TEST/RETEST DATA COMPARISIONS

THE FOLLOWING DATA SPREAD SHEETS ARE THE RESULT OF "IN-HOUSE" TESTING TO DETERMINE THE ACCURACY OF TEST RE-TEST ON THE SAME BIO-OHM METRE THE SUBJECTS WERE CHOOSEN FROM PATIENTS OF "LIVING WELL" IN TIGARD, OREGON.

GROUP B:

| Subject | Sex | Age | Height | Weight | Test I | Re-Test |
|---|---|---|---|---|---|---|
| 1 | M | 23 | 70.0 | 166 | 490 | 487 |
| 2 | M | 20 | 76.0 | 199 | 388 | 382 |
| 3 | M | 31 | 73.0 | 217 | 423 | 423 |
| 4 | M | 25 | 69.0 | 201 | 376 | 378 |
| 5 | M | 23 | 71.5 | 223 | 354 | 348 |
| 6 | M | 22 | 70.0 | 188 | 433 | 433 |
| 7 | M | 19 | 65.3 | 175 | 387 | 387 |
| 8 | M | 20 | 69.0 | 163 | 489 | 492 |
| 9 | M | 27 | 71.5 | 198 | 422 | 417 |
| 10 | M | 22 | 65.4 | 167 | 354 | 354 |
| 11 | M | 21 | 67.75 | 156 | 367 | 367 |
| 12 | M | 21 | 71.5 | 211 | 405 | 407 |
| 13 | M | 23 | 73.75 | 189 | 381 | 378 |
| 14 | M | 19 | 70.0 | 176 | 361 | 361 |

FEMALES:

| | | | | | | |
|---|---|---|---|---|---|---|
| 1 | F | 31 | 65.5 | 133 | 623 | 625 |
| 2 | F | 26 | 67.5 | 143 | 665 | 664 |
| 3 | F | 30 | 62.0 | 112 | 544 | 521 |
| 4 | F | 23 | 65.25 | 119 | 567 | 567 |
| 5 | F | 21 | 61.0 | 103 | 707 | 705 |
| 6 | F | 19 | 58.75 | 92 | 772 | 771 |
| 7 | F | 20 | 65.5 | 144 | 615 | 612 |
| 8 | F | 20 | 66.0 | 132 | 598 | 602 |
| 9 | F | 23 | 68.5 | 123 | 576 | 580 |

STANDARD INDIVIDUAL ERROR: 1.5 OHMS

*Individual Sessions Same Day

*FIG. 10*

DATA LIST STATEMENT & TABLE

DATA LIST FILE = RAW/ID 1-3 SEX 5 HEIGHT 9-12 (2) RACE 7
WGTKGS 13-17 (2) H2OFAT 19-21 (1)
IMPFAT 31-33 (1) C1 35-36 C2 TO C5 37-48
C6 TO C11 49-60 C12 61-63 C13 TO C14 64-67

| | | |
|---|---|---|
| 1 | 0 | |
| 2 | 0 | |
| 3 | 0 | |
| 4 | 0 | |

THE ABOVE DATA LIST STATEMENT WILL READ 1 RECORDS FROM FILE RAW

| VARIABLE | REC | START | END | FORMAT | WIDTH | DEC |
|---|---|---|---|---|---|---|
| ID | 1 | 1 | 3 | F | 3 | 0 |
| SEX | 1 | 5 | 5 | F | 1 | 0 |
| HEIGHT | 1 | 9 | 12 | F | 4 | 2 |
| RACE | 1 | 7 | 7 | F | 1 | 0 |
| WGTKGS | 1 | 13 | 17 | F | 5 | 2 |
| H2OFAT | 1 | 19 | 21 | F | 3 | 1 |
| IMPFAT | 1 | 31 | 33 | F | 3 | 1 |
| C1 | 1 | 35 | 36 | F | 2 | 0 |
| C2 | 1 | 37 | 39 | F | 3 | 0 |
| C3 | 1 | 40 | 42 | F | 3 | 0 |
| C4 | 1 | 43 | 45 | F | 3 | 0 |
| C5 | 1 | 46 | 48 | F | 3 | 0 |
| C6 | 1 | 49 | 50 | F | 2 | 0 |
| C7 | 1 | 51 | 52 | F | 2 | 0 |
| C8 | 1 | 53 | 54 | F | 2 | 0 |
| C9 | 1 | 55 | 56 | F | 2 | 0 |
| C10 | 1 | 57 | 58 | F | 2 | 0 |
| C11 | 1 | 59 | 60 | F | 2 | 0 |
| C12 | 1 | 61 | 63 | F | 3 | 0 |
| C13 | 1 | 64 | 65 | F | 2 | 0 |
| C14 | 1 | 66 | 67 | F | 2 | 0 |

END OF DATALIST TABLE

*FIG. 15*

SYSTEM FOR BODY IMPEDANCE DATA ACQUISITION

BACKGROUND OF THE INVENTION

This invention relates to a system for conveniently and accurately measuring and quantitating the conductive potential of a human body which is based on a determination of lean tissue content.

Obesity has truly been declared, as of 1985 by the National Institute of Health, a stand-alone risk factor. In fact, obesity has been declared as a disease unto itself. It is now a new medical standard that obesity needs to be diagnosed and treated by a physician for the health and well-being of the general public.

A true definition of "obesity" has been difficult to define, in that such definition is dependent upon a percent body fat determination.

Historically, "percent body fat" has been determined in research laboratories by dunking people in a hydrostatic tank to perform a hydrostatic critereon method for quantification of body fat.

Hydrodensitometry (water tank immersion) has been generally considered to be the traditional standard for body composition analysis. Despite the biological and experimental errors inherent in hydrodensitometry (Lohman, T. G., Skinfolds and Body Density and Their Relation to Body Fatness: A Review, *Human Biology*, 53: 181-225), all other methods of analysis must be compared to it if they are to be validated.

Another known method for body fat analysis is skinfold anthropometry (calipers). However, many skilled health care practitioners have questioned this methodology for body composition analysis in that reliability is doubtful. In the hands of trained technicians, anthropometry can give errors of plus or minus nine percent (9%) when compared to densitometry (Katch, F. I., Katch, V. L. (1980), Measurement and Prediction Errors in Body Composition Assessment and the Search for the Perfect Equation. *Research Quarterly for Exercise and Support*, Vol. 51, No. 1, 249-260). In general clinical use in the hands of a variety of trained examiners with less than expert skill, the error in the caliper technique is presumably even greater.

Recently, body composition analyzers have been introduced that utilize a relatively new technology known as tetrapolar bioelectrical impedance.

Most importantly, through tetrapolar bio-electrical technology, the test/retest reliability has been reported as 0.5% (Lukaski, H. C., Johnson, P. E., Bolonchuck, W. W., and Lykken, G. I., Assessment of Fat-Free Mass Using Bio-Electrical Impedance Measurements of the Human Body) compared to a test/retest reliability of 3.8% for hydrodensitometry.

In this respect, the human body is composed basically of two components—one is lean body mass, which is composed of muscle tissue, connective tissue and bones; and the other major component is body fat. Bio-electrical impedance technology quantifies the true ratio of these components—the difference between lean body mass, which is the healthy metabolising part, and the body fat, which is the storage of energy in your body. Lean body mass has about 75% water; in contrast, fat is about 3% to 13% water. Accordingly, bio-electrical impedance technology measures the "healthy" part of the body, which is the lean body mass.

While known tetrapolar bio-electrical technology is considered by many to be an advance from hydrodensitometry, both from a reliability standpoint and convenience standpoint, known systems have produced inaccurate body composition analysis in that such known systems are dependent upon a linear regression equation approach. Moreover, much of the data derived from known bio-electrical impedance techniques fails to consider biological data of specific patient groups which may deleteriously affect the accuracy of the body composition analysis.

Accordingly, those skilled in the art have recognized a significant need for an accurate, valid measurement approach of human body composition. The present invention provides a procedure for quantitative measurement of the conductive potential of the body in a convenient and reliable manner and then provides the means for modifying that body impedance measurement with algorithm formula equations that generate scientifically validated predictions of human body composition analysis. The present invention fulfills these needs.

SUMMARY OF THE INVENTION

The unique system of the present invention provides an accurate valid measurement of human body composition consisting of fat tissue, lean tissue and body water. The inventive methodology provides a procedure for quantitative measurement of the conductive potential of the body, which is based on the lean tissue content of the body, in a convenient and reliable manner.

In more detail, the quantitative measurement in accordance with the present invention is referred to as a "bio-impedance signal." This electrical signal, in ohms, is derived from a means for measuring body impedance component of the system. The resultant signal (three digit number, between 1 and 1000 ohms) is then entered into a modifying means component to accurately predict the body composition of the tested individual.

The unique modifying means, in one embodied form, comprises prediction formulas derived from biological data inputs including: a patient's height, weight, age and sex, to determine a "population prediction variable derived from the impedance signal modified by a prescribed correlation factor of body density described herein."

Thus, the unique modifying means of the inventive system interprets bio-impedance readings as "population specific", i.e., specific impedance values are exhibited by various pre-defined populations of individuals. This specificity is related to morph-type, leanness, body water and age. In accordance with the present invention, an algorithm formula approach to prediction formulas is utilized to define an appropriate individual into a set of population specific variables.

Initially, the bio-impedance signal is imputed into the modifying means along with biological data. Thereafter, algorithm formulas modify the inputted signals by the appropriate correction factor. The correction factor is generally non-linear and derived from comparison with known hydrostatically derived values to produce an output which may then be conveniently displayed by indicator means so that body composition can be predicted.

It will be appreciated from the foregoing that the present invention provides an accurate and convenient system for quantifying body fat as a percentage of weight which is an important health management tool for patient and physician alike. Other features and advantages of the present invention will become apparent from the following, more detailed description, taken in conjunction with the accompanying drawings, which illustrate by way of example the principles of the invention.

BRIEF DESCRIPTION OF THE DRAWINGS

FIG. 9 is a perspective view of a suitable computer in accordance with one embodiment of the present invention;

FIG. 10 is a chart of tests/re-test data comparison in accordance with the present invention;

FIG. 11 is a chart of inter-meter comparisons in accordance with the present invention;

FIG. 15 is a graph which reflects the male component of the sample referred to in Example in accordance with the present invention.

DESCRIPTION OF THE PREFERRED EMBODIMENTS

Figure 1:
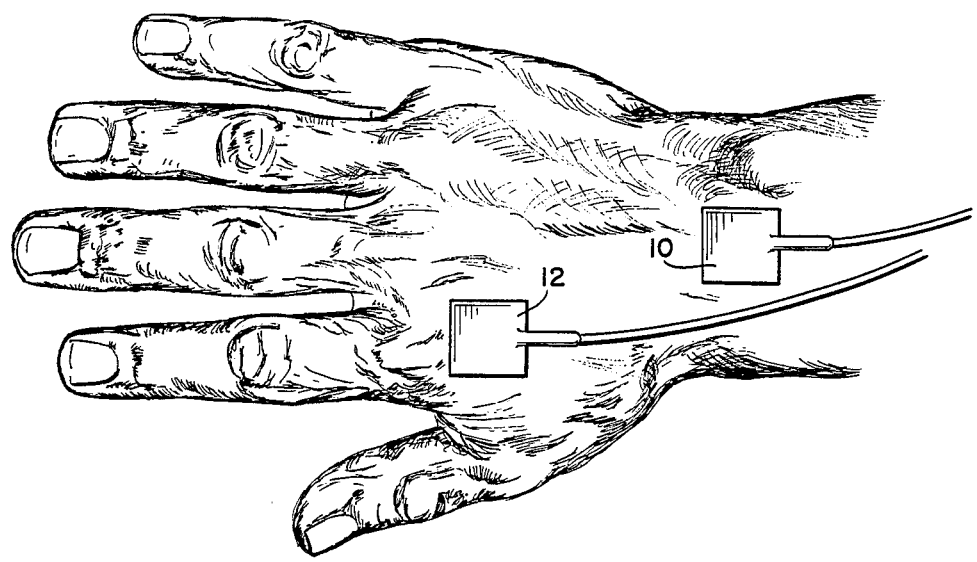
FIG. 1 is a perspective view of first and second prescribed locations for locating electrode sensors in accordance with one embodiment of the present invention.

As shown in the drawings for purposes of illustration, the present invention is embodied in a unique system for acquisition of body impedance date, which comprises in combination:

(a) a plurality of electrode sensors for mounting to prescribed locations of a patient's body to be analyzed;

(b) mounting means for removably attaching said electrode sensors to a Kelvin Bridge bio-impedance meter system having four terminal leads;

(c) means for generating a current flow through said electrode sensors at a frequency of from about 40 Kilohertz to about 60 Kilohertz, thereby producing an output range of 0 to 1,000 ohms;

(d) means for generating input variables comprised of biological patient data including, height, weight, age, and sex and bio-impedance signal to determine a population specific variable;

(e) means for manipulating said electrical signals derived from said means for generating a body impedance signal with said population prediction variable;

(f) indicator means for displaying said resultant output signal to provide quantitative measurement of conductive potential of said patient's body based on lean tissue content of said patient; and (g) means for comparing said resultant signal with known scatter grams to produce an output signal representative of fat tissue, lean tissue and body water.

In accordance with the present invention, an electrical Kelvin Bridge is created by a plurality of electrodes which are removably attached to specific body areas. In more detail, prior to sensor placement, each body location is palpated and preferably cleaned with an alcohol swab to remove skin or surface oils. Thereafter, each electrode sensor is placed on a patient's body. Preferably, a conductive gel is utilized to temporarily hold the sensor in place.

ELECTRODE SENSOR LOCATIONS (1) The first prescribed location 10 is the back side of the patient's right hand. ("Dorsal Aspect.") Locate the "Styloid Process." (The 'bump' near the back of the wrist.) Palpate approximately 0.5 to 1 inch directly across from the "Styloid Process." (Note the slight 'depression' between the "Radius" and "Ulna.") The First Sensor is placed across from the "Styloid Process" in the middle of the wrist. (The Sensor center should be directly over the slight 'depression' described above.) Note: Placing the electrodes so they 'point' away from the body is recommended. (See FIG. 1)

(2) The second prescribed location 12 is behind the knuckle (joint) of the index finger of the right hand. ("Distal end of the second metacarpal.") Palpate this area. Place the Second Sensor directly on the hand behind, but not touching, the right index finger. (See FIG. 1)

Figure 2:
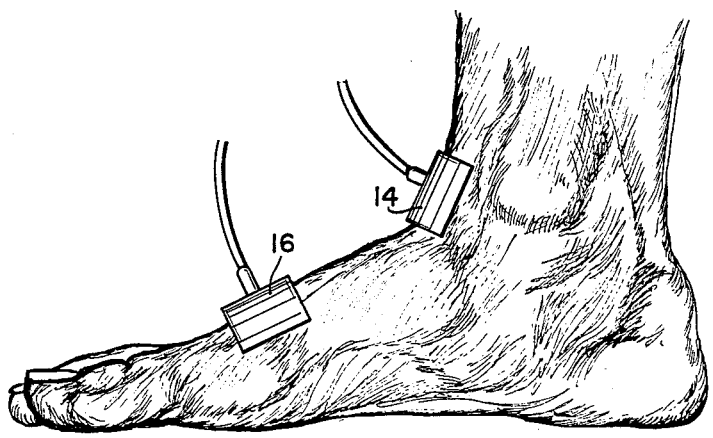
FIG. 2 is a perspective view of second and third prescribed locations for locating electrode sensors in accordance with one embodiment of present invention.

(3) The third prescribed location 14 is the patient's ankle at the front of the right foot. (In between the "Medial" and "Lateral Malleoli"--the 'bumps' on the inside and outside of the ankle.) Note the slight 'depression' in this area where the ankle meets the top of the foot. Palpate here. Place the Third Sensor so that its center directly covers the slight 'depression' described above. (See FIG. 2)

(4) The fourth prescribed location 16 is the top of the right foot behind the joint of the great toe. (The "Distal" portion of the first "metatarsal.") Palpate this area. Place the Fourth Sensor on the top of the right foot, behind, but not touching the great toe. (See FIG. 2)

POWER SUPPLY

Figure 3:
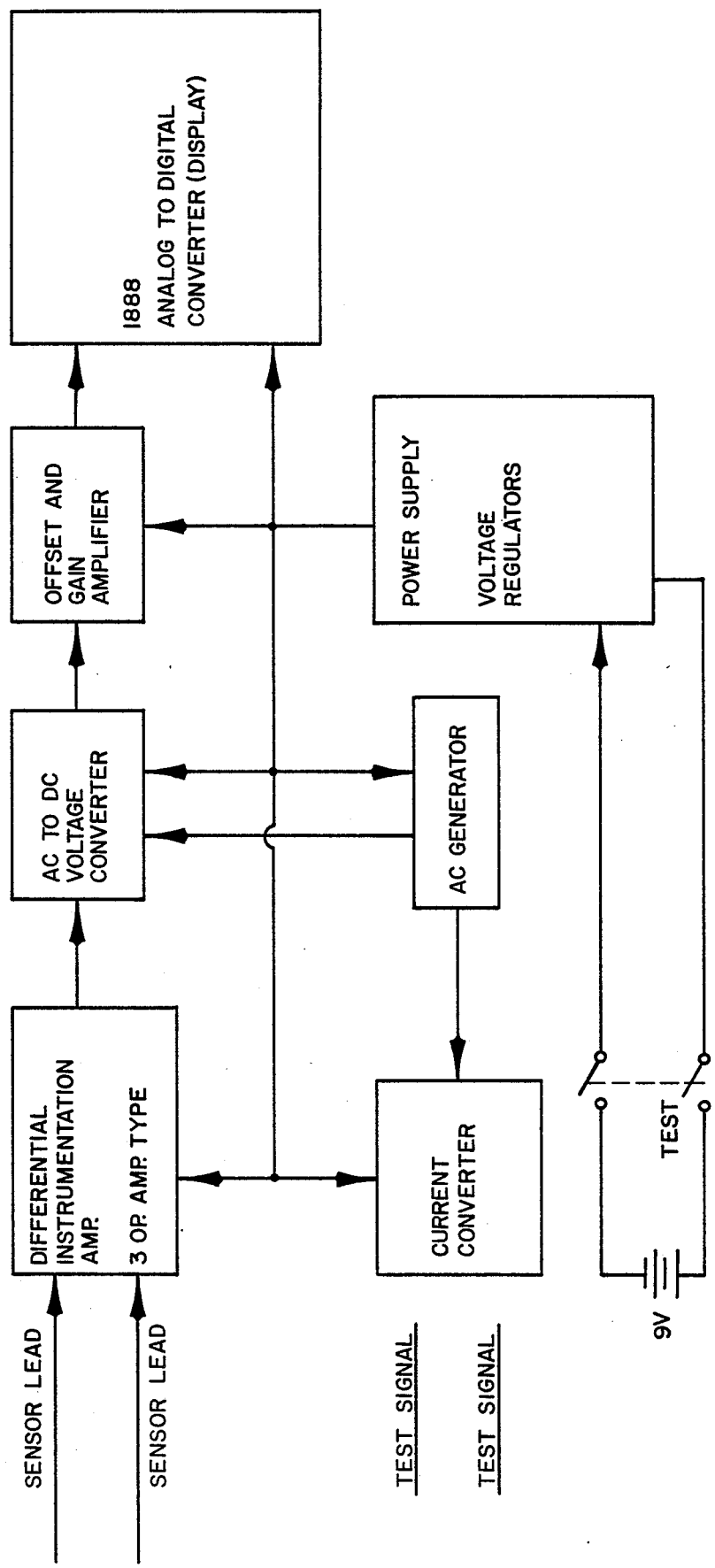
FIG. 3 is a schematic block diagram depicting one embodied form of the inventive system for body impedance data acquisition in accordance with the present invention.
Figure 5:
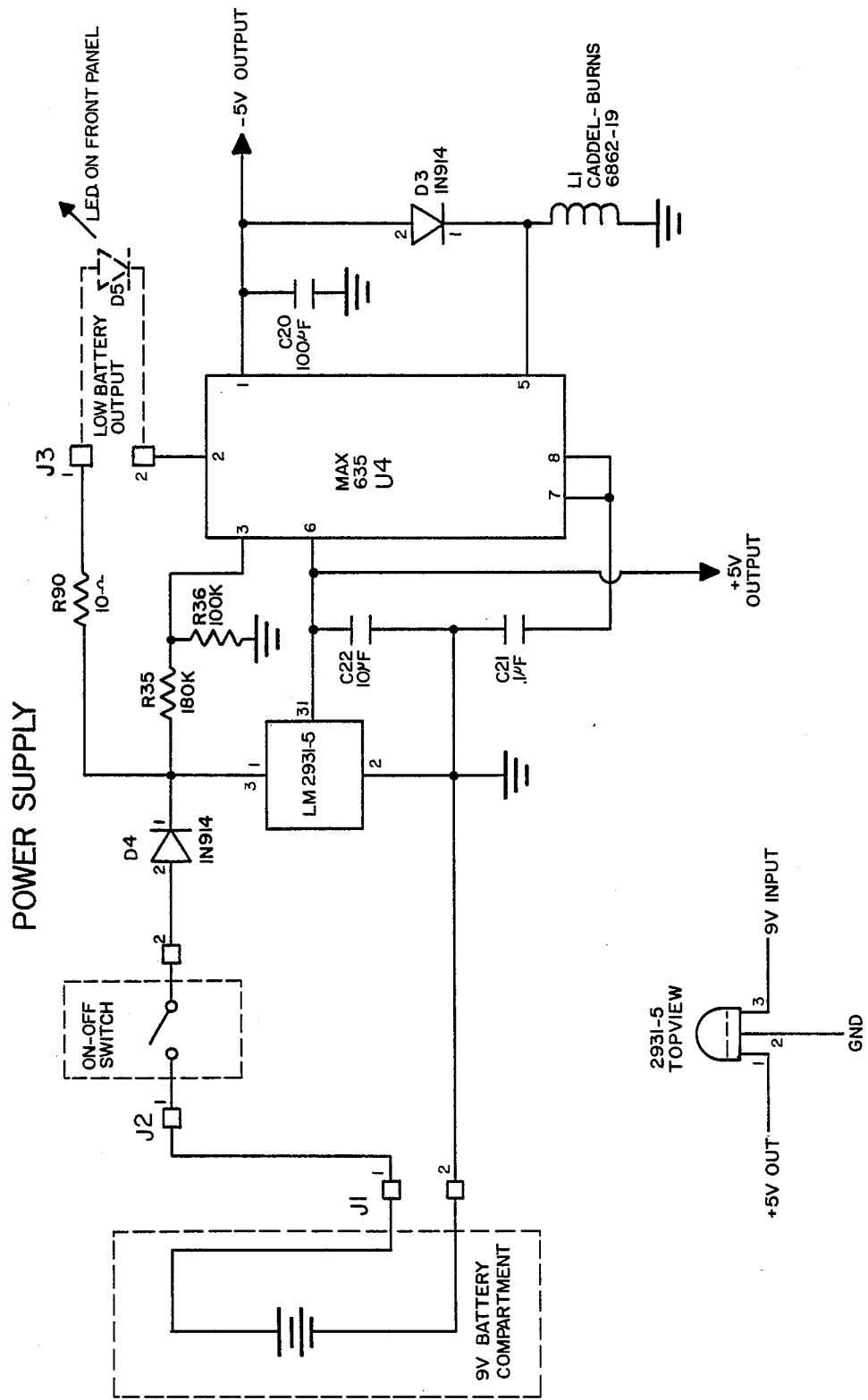
FIG. 5 is a circuit diagram of a power supply for the inventive system in accordance with one embodied form of the invention.

The power supply for the inventive system is preferably provided by a single nine (9) volt alkaline battery (See FIGS. 3 and 5). The circuit pathways are designed for safety and efficiency. A momentary on and off power switch is used to conserve battery life. The bio-impedance meter test life expectancy is 500 tests.

The design of the power supply circuit allows a test signal and a sensor circuit to operate within given parameters without being dependent upon a specific battery change level. Diode protection is preferably provided both at the power source and at the power input section of the printed circuit board to insure against reverse current flow.

To maintain an optimal functioning range, the system generates a 5 volt charge to power the sensor and digital functions.

To provide a reliable and viable power source, a low battery (LED) is displayed when the current power source (9 volt battery) drops below 6.2 volts.

The power drain of the LED will consume the remaining voltage within 30 seconds. Note: The average commercial grade 9 volt alkaline battery is charged at 9.2 volts.

MEANS FOR GENERATING BODY IMPEDANCE SIGNAL

Preferably one 9-volt battery operates the means for generating body impedance signal. The technology utilizes a Kelvin Bridge system with 4 terminal leads. The Sensors previously described attaches to each terminal end and is placed on the patient for correct data Impedance acquisition.

OPERATION

As described, the body impedance system generates a frequency which is totally undetectable to the human body.

After checking that the four electrode sensors are properly placed, the patient remains prone and still.

The on/off switch is placed in the "on" position. The Meter takes Impedance readings at a rate of 50,000 times per second. Often the Meter takes 1 to 3 seconds to stabilize while 'searching' for the most accurate reading. Several factors such as subcutaneal fat thickness, skin thickness and body hair account for slower impedance readings.

TECHNICAL SPECIFICATIONS

The preferred technical specifications of the means for generating body impedance system are as follows:

| (a) Device test signal current nominal; | about 800 microamps |
|---|---|
| (b) Device test signal frequency | about 50 KHZ nominal; |
| (c) Input range | 0 to 1000 ohms; |
| (d) Input impedance | about 10 meg ohm; |
| (e) Accuracy | about 1%; |
| (f) Supply current (qeiecent) | about 70 MA nominal; |
| (g) Negative supply battery range | about 8.5 to 10 volts; |
| (h) Positive supply battery range | about 8.5 to 10 volts; |
| (i) Battery polarity protection | Dual diode. |

SCHEMATIC DIAGRAM

Figure 7:
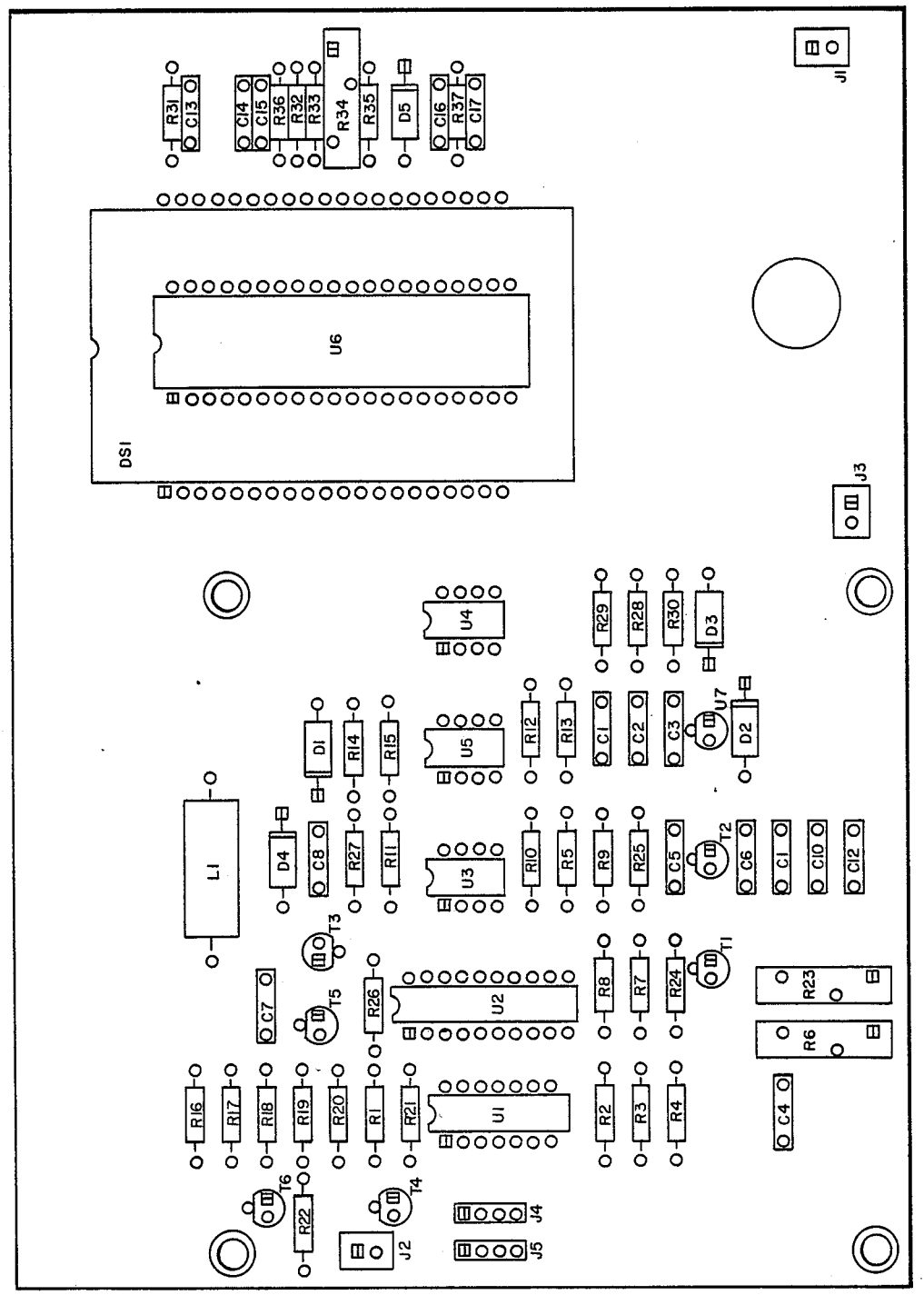
FIG. 7 is an electrical circuit diagram of a pin-out diagram of a body impedance meter in accordance with one embodiment of the present invention.

The pin-out diagram illustrated in FIG. 7 details one embodied printed circuit board for the means for generating body impedance system.

The details of the schematic are presented in the following sections:
 (1) Sensor circuit; and
 (2) Test signal generation.

Each of these sections will refer to block diagrams to highlight the exact electronic configuration.

SENSOR CIRCUIT

Figure 6:
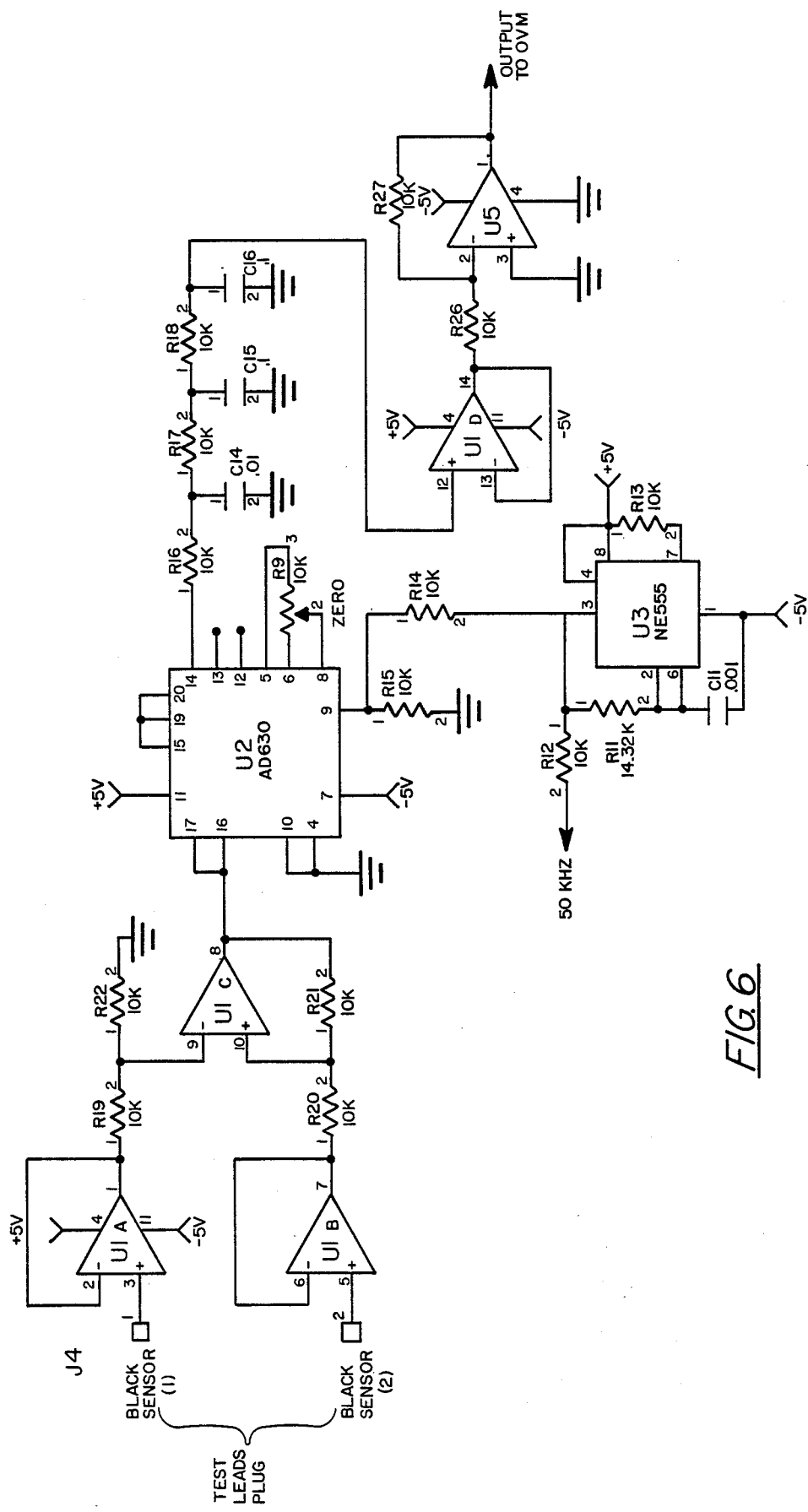
FIG. 6 is a circuit diagram of a sensor circuit in accordance with one embodied form of the present invention.

FIGS. 3 and 6 are block diagrams detailing one embodied sensor circuit of the impedance meter. The electronic circuitry and components include the analog to digital (A to D) technology. To obtain valid bio-impedance measurements, a true tetra-polar bridge system must be employed. The circuit in application provides a tetra-polar bridge (four lead bridge).

The sensor circuit preferably operates at an 800 microamp level. The sensor current combined with the test signal generation, powers the inventive system.

As outlined previously, the bio-impedance analyzer is connected to the body by four leads, two connected to the right hand and two to the right foot. The sensing current is then placed between the poles.

TEST SIGNAL GENERATION

Figure 4:
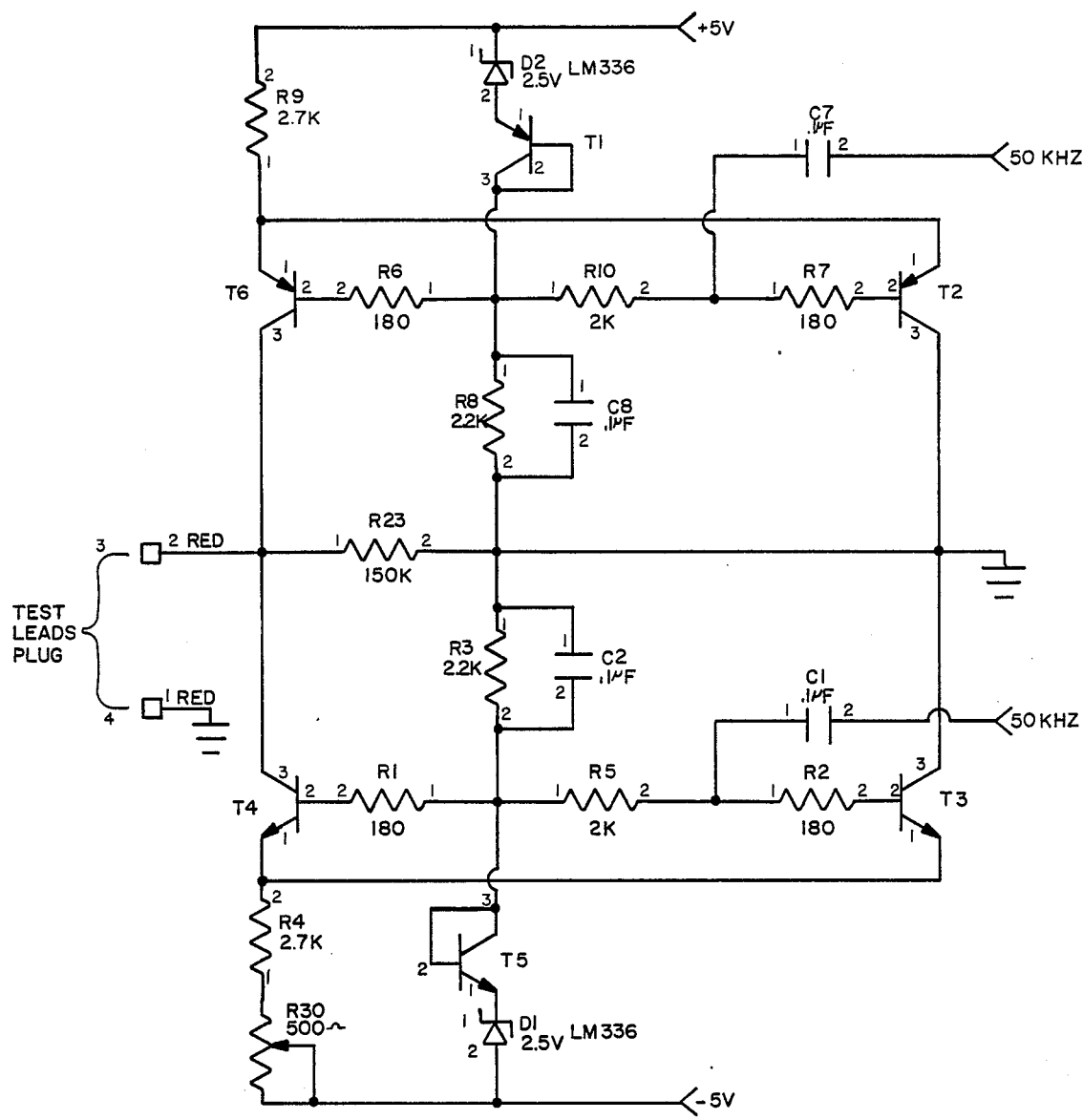
FIG. 4 is a circuit diagram of a test signal generator in accordance with one embodiment of the present invention.

A test signal is maintained through the components with a frequency of between 40 to 60 Kilohertz and preferably at 50 KiloHertz. The block diagram illustrated by FIGS. 3 and 4 details the specifications and current flow of the bio-impedance analyzer. The test signal configuration is calibrated at the 500 ohms level, selected as a mid-point in the bio-impedance analyzer reading scale of 1 to 1000 ohms.

The test signal generator remains constant due to the constant voltage of 5 volts from the power supply. A constant power supply of 5 volts is critical for the reproducability of data obtained from the bio-impedance analyzer. A low battery indicator calibration for 6.2 volts ensures a constant 5 volt current source.

MODIFICATION OF IMPEDANCE SIGNALS BY POPULATION SPECIFIC VARIABLE

The raw electrical signals from the impedance meter are modified by a prescribed correlation factor of body density.

$$(BD = 1.14111 - 0.0763 \text{ (weight)} \text{ (impedance/height}^2\text{)}.$$

Based on a given body density a "range of impedance readings" is expected. This range is population specific. Thus, once body density is derived and compared to impedance, a constant is then selected for the body analysis formula.

Figure 8:
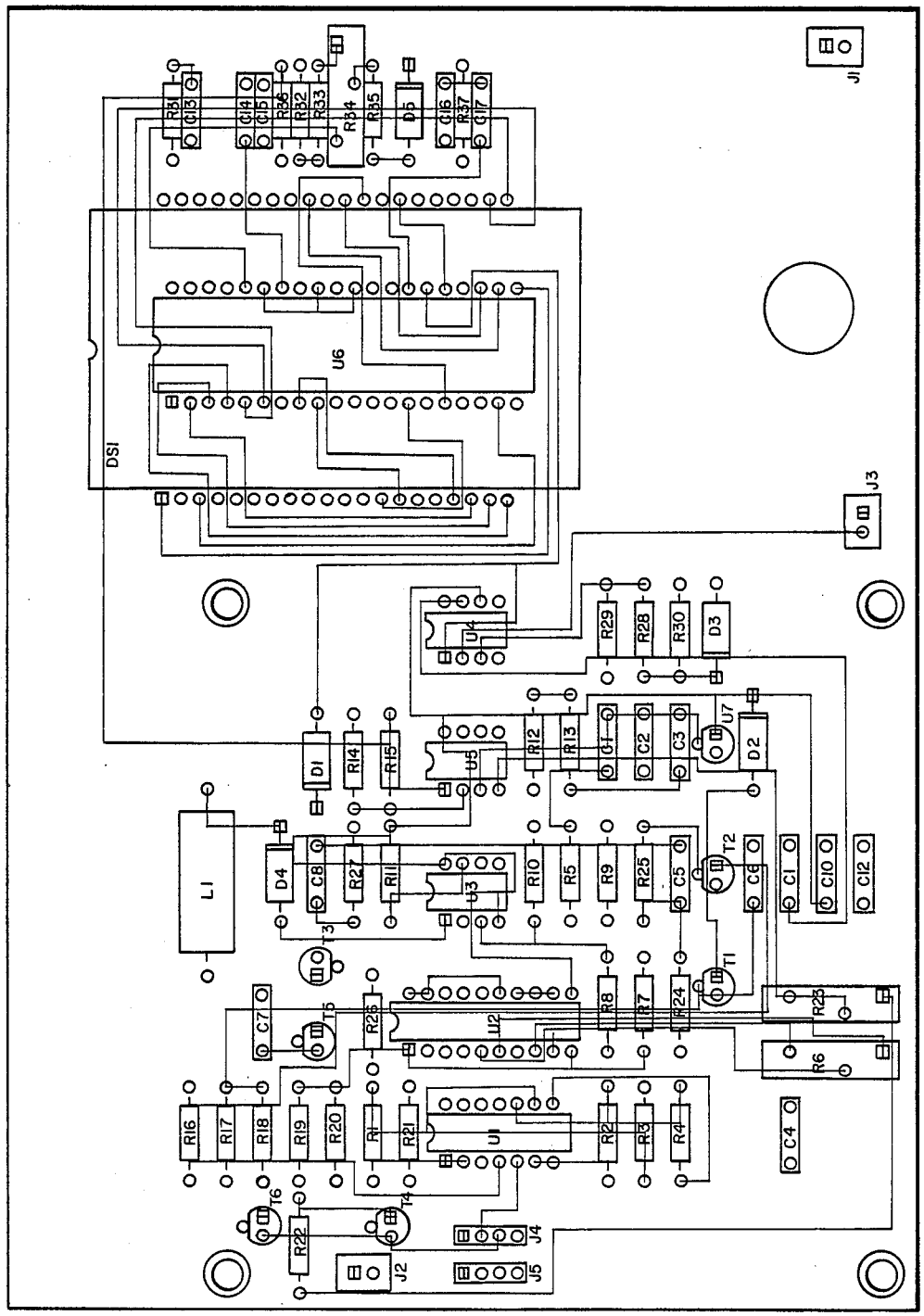
FIG. 8 is a schematic in more detail of a body impedance meter in accordance with one embodiment of the present invention.
Figure 12:
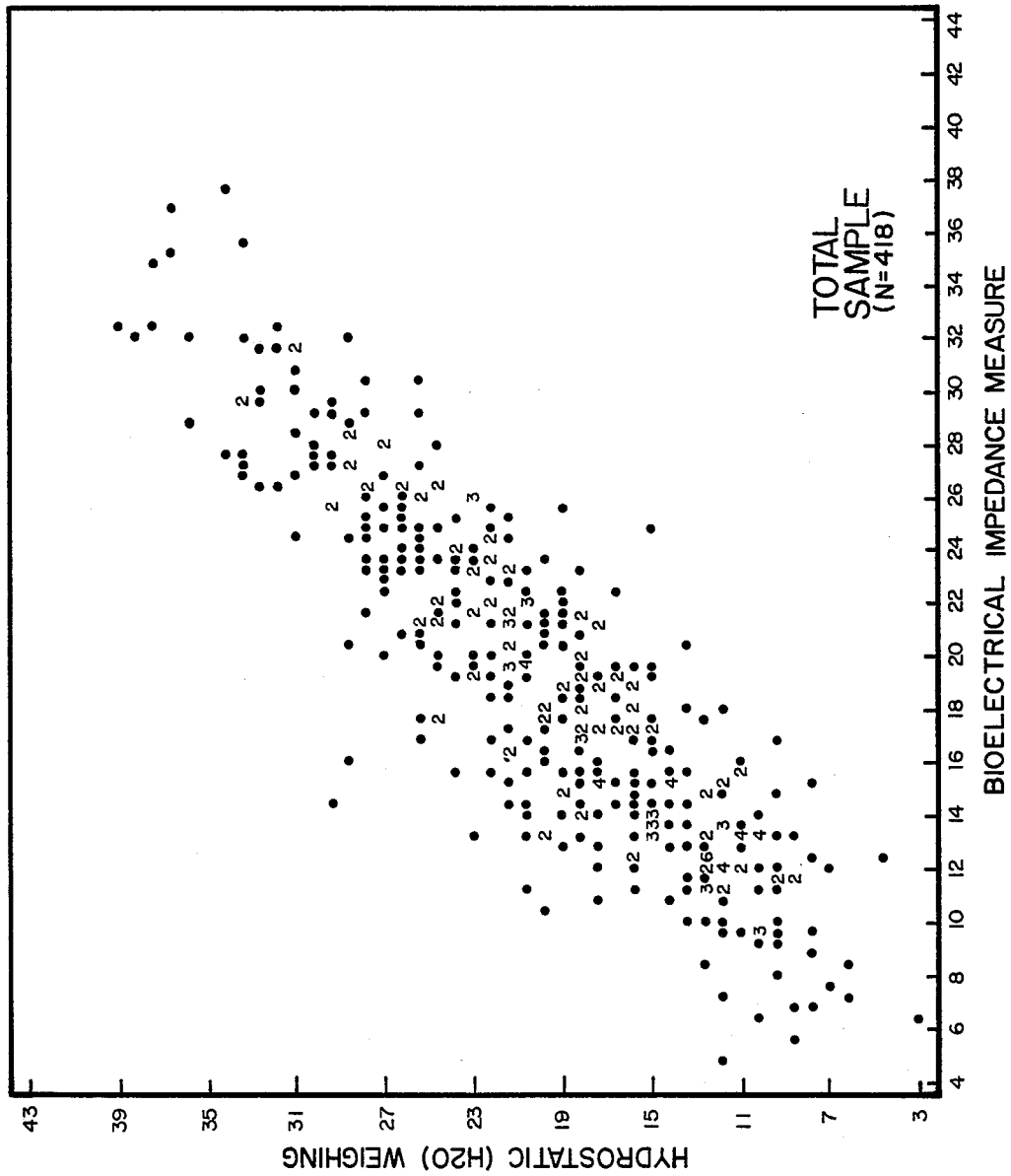
FIG. 12 is a graph which reflects the total sample referred to in Example I in accordance with the present invention.
Figure 13:
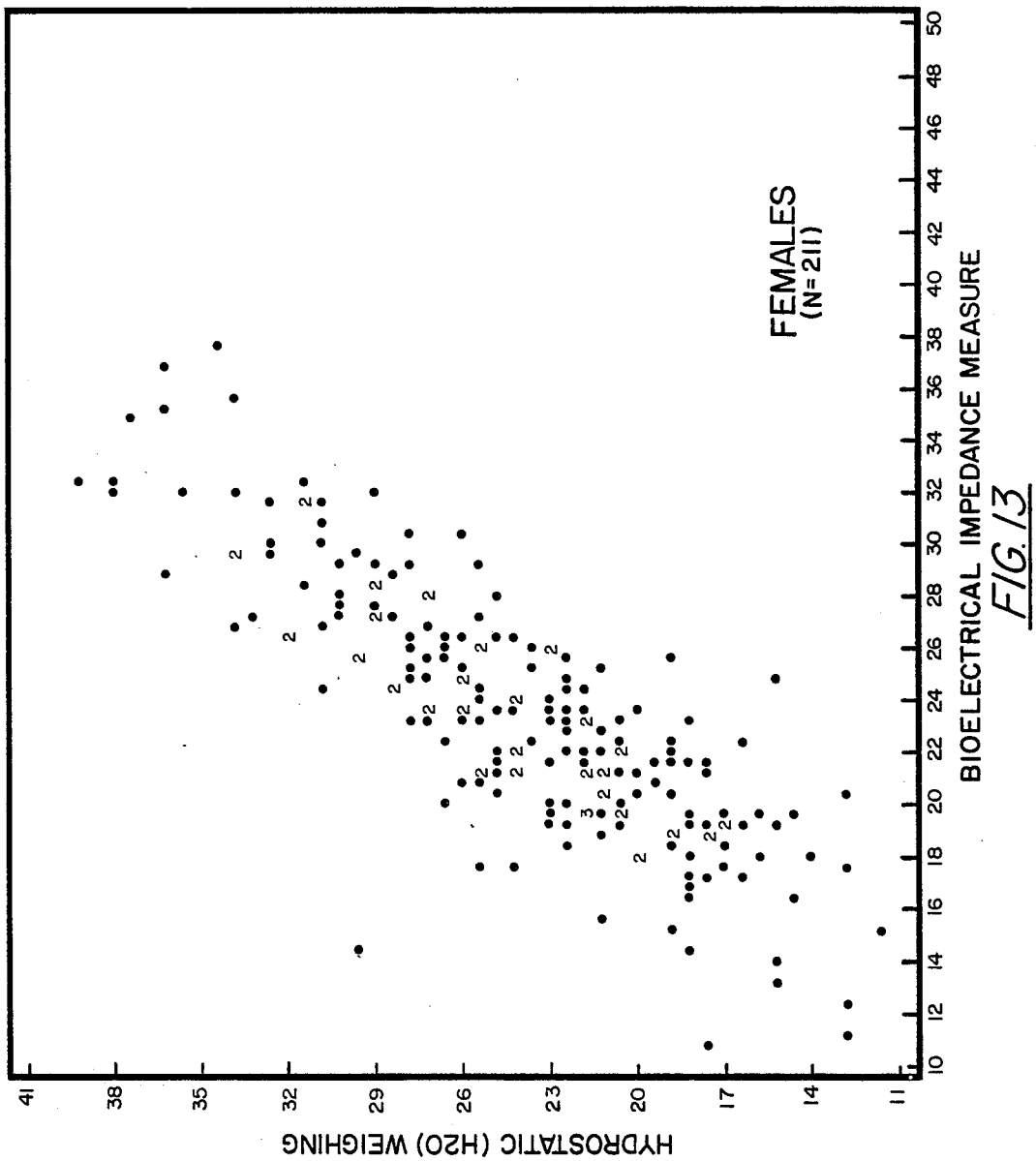
FIG. 13 is a graph which reflects the female component of the total sample referred to in Example I in accordance with the present invention.
Figure 14:
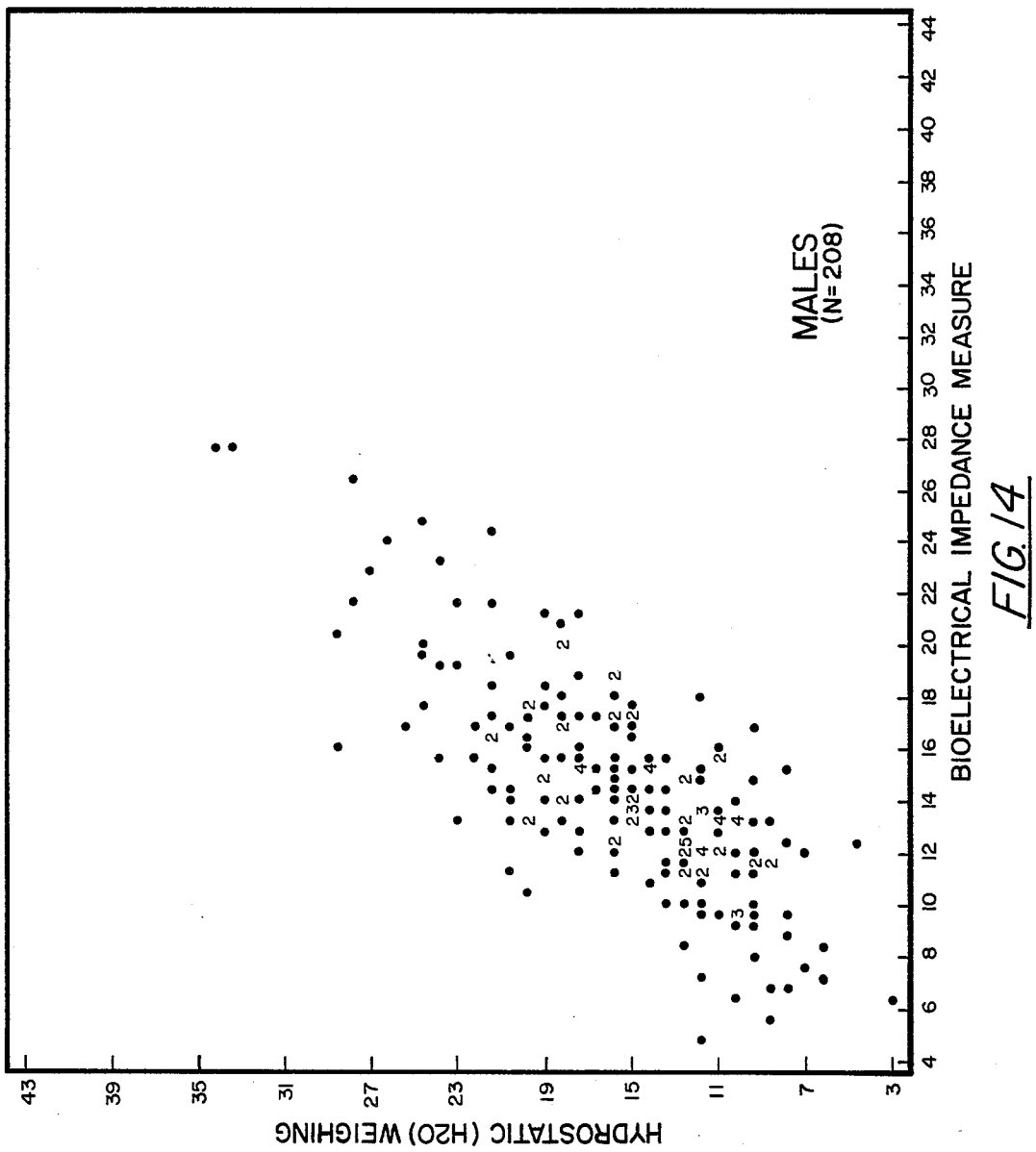
FIG. 14 is a data list statement and data list table for the graph referred to in the ILLUSTRATIVE Examples in accordance with an embodiment of the present invention.

FIG. 8 represents one embodied individual progression through a population prediction formula.
 (a) Biological data input:
  (1) Bio-impedance
  (2) Age
  (3) Height
  (4) Weight
  (5) Sex
 (b) Algorithm formula determination of body analysis formula constant based on body density and impedance:
  e.g. If body denisty is ( 1.9 and impedance (400 then
$$X = 2.835$$
Note: X is the body analysis formula constant.
 (c) Population Prediction formula:

After phase one (a) and two (b) are complete, the main prediction formula which has been modified by the algorithm analyzes the data to predict body composition.

e.g. Percent fat $= (4.95 / x - 4.5)$

Note: X is the constant from the algorithm.

The inventive system preferably includes an attached microprocessor to perform the data processing tasks for body composition testing and analysis. The Computer desirable and has capacity for expandable features. (See FIG. 9)

Preferably the Computer is permanently mounted and cannot be removed from a transport case. A 6 volt adapter may be used to power the micro-processor.

INDICATOR MEANS FOR DISPLAYING DATA

Preferably a Printer such as OKI-DATA 182 microline is utilized in the system. A brief explanation for operation is provided herein.

TEST PROCEDURE

Height/Weight and Proper Patient Position (1) Record patient's height and weight. (Height in inches, weight in pounds.) Do not use data supplied by patient. Accurate height and weight measurements are essential for accurate results. Remove patient's shoes for both measurements. Also remove the sock/hose on the right foot. (The site for distal electrode sensor placement.)

(2) Position the patient prone on a non-conductive surfaced table. Do not test a patient lying on a tile or carpeted floor. Statis electricity contained in these surfaces interferes with accuracy. The patient must be prone to minimize interference from muscle contractions. (Antagonist muscle contractions in standing or sitting patients create inaccurate Impedance results.)

(3) Arrange the patient's limbs so they are slightly apart, hands not touching the torso, feet not touching each other.

OPERATION CHECK LIST (a) Attach Electrode Sensors to Patient Lead Cables.
(b) Remove Patient's shoes and right sock/hose.
(c) Measure Patient's height.
(d) Weigh patient.
(e) Record Patient Height and Weight on Patient Data Form.
(f) Place Patient prone on table.
(g) Palpate Electrode Sensor locations.
(h) Place Electrode Sensors to right hand and right foot.
(i) Collect Patient Impedance reading.
(j) Record Impedance reading on Patient Data Form.
(k) Select program on the Main Menu and ENTER.
(l) ENTER information needed for Patient Data Input.
(m) Remove Printout from the Printer.

ILLUSTRATIVE EXAMPLES

The following specific examples will be helpful to a clearer understanding of the unique features of the present invention:

EXAMPLE I

A study was conducted to evaluate the validity of bioelectrical impedance as an accurate assessment of body composition. Two-hundred and forty nine male and female volunteers from the University of Southern California were used as subjects. Each subject reported to the Exercise Physiology lab at USC in a normally hydrated state. Body composition evaluation was made by hydrostatic weighing (H20) and bioelectrical impedance (Imp). Hydrostatic weighing was done in a seated position in a 1000 gallon tank using a Chatillon autopsy scale. A minimum of 5 trials was made on each subject. Residual lung volume was measured utilizing the oxygen dilution technique and employing a Hewlett-Packard Nitrogen analyzer. Body fat was calculated using the formula of Brozek, et al. (4.57/Density 4.142 ×100%). Bio-electrical impedance was measured on each subject employing the standard procedures for the technique. Average body fat for the males (N=117) was 14.1% measured by H20 and 14.3% as measured by Imp. The validity coefficient for this group was r=−0.78 and the standard error of estimate (SEE) was 3.07%. The corresponding values for the female group (N=132) were follows: Average body fat from H20 =23.5%; from Imp =23.3%; validity coefficient, r =0.80; SEE =2.879%. The results of the present study support the use of the bio-electrical impedance technique as a method of assessing body composition in normal, healthy individuals. (See FIGS. 10 through 15)

EXAMPLE II

A study was conducted to evaluate the validity of bioelectrical impedance as an accurate assessment of body composition. Four-hundred and eighteen male and female volunteers from the University of Southern California were used as subjects. Each subject reported to the Exercise Physiology lab at USC in a normally hydrated state. Body composition evaluation was made by hydrostatic weighing (H20) and bioelectrical impedance (Imp.) [BioAnalogics - "Consultant" System] Hydrostatic weighing was done in a seated position in a 1000 gallon tank using a Chatilon autopsy scale. A minimum of 5 trials was made on each subject. Residual lung volume was measured utilizing the oxygen dilution technique and employing a Hewlett-Packard Nitrogen analyzer. Body fat was calculated using the formula of Brozek et. al. (4.57/Density - 4.142 ×100%). Bio-electrical impedance was measured on each subject in a supine position. Average body fat for the male (N=208) was 15.2% measured by H20 and 14.4% as measured by Imp. The range of body fat for this group was 3-35%. The validity coefficient for this group was r =0.76 and the standard error of estimate (SEE) was 3.34%. The corresponding values for the female group (N=211 ) were as follows: Average body fat from H20 =23.9%; from Imp =23.4%; range =11-39%; validity coefficient, r =0.83; SEE =3.15%. The results of the present study support the use of the bio-electrical impedance technique as a method of assessing body composition in normal, healthy individuals.

Accordingly, the unique system of the present invention provides an accurate valid measurement of human body composition consisting of fat tissue, lean tissue and body water. The inventive methodology provides a procedure for quantitative measurement of the conductive potential of the body, which is based on the lean tissue content of the body, in a convenient and reliable manner. Although a preferred embodiment of the invention has been shown and described, it will be apparent that other adaptation and modifications can be made without departing from the spirit and scope of the invention. Accordingly, the invention is not to be limited, except as by the following claims.

We claim:

1. A system for acquisition of body impedance data quantitative measurement of the conductive potential of the body, the system comprising in combination:
   (a) a plurality of electrode sensors for mounting to a patient's body to be analyzed at prescribed locations forming a tetrapolar system;
   (b) mounting means for removably attaching said electrode sensors to a Kelvin Bridge bio-impedance meter system having four terminal leads;

(c) means for generating a current flow through said electrode sensors at a frequency of from about 40 Kilohertz to about 60 Kilohertz, thereby producing an output range of from about 0 to 1,000 ohms;

(d) means for accepting input variables comprised of biological patient data including, height, weight, age and sex and bio-impedance signals derived from step (c) to determine a population specific variable and to produce a correspondence electrical signal;

(e) means for manipulating electrical signals derived from said means for generating a current flow and said means for accepting input variables to produce a resultant output signal; p1 (f) indicator means for displaying said resultant output signal to provide quantitative measurement of conductive potential of said patient's body based on lean tissue content of said patient; and (g) means for comparing said resultant output signal with a control signal to produce an output representative of fat tissue, lean tissue and body water.

2. The system for body impedance data acquisition as defined in claim 1, wherein one of said electrode sensors is mounted on the dorsal aspect of the patient's right hand.

3. The system for body impedance data acquisition as defined in claim 1 wherein one of said electrode sensors is mounted at the distal end of the second metacarpal of the patient's right hand.

4. The system for body impedance data acquisition as defined in claim 1, wherein one of said electrode sensors is mounted in between the medial and the lateral malleoli of the patient's right foot.

5. The system for body impedance data acquisition as defined in claim 1, wherein one of said electrode sensors is mounted at the distal portion of the first metatarsal of the patient's right foot.

6. The system for body impedance data acquisition as defined in claim 1, wherein said means for generating a current flow operates at a frequency of about 50 kilohertz.

7. The system for body impedance data acquisition as defined in claim 1, and further comprising a power supply for the system.

* * * * *